US006497699B1

(12) United States Patent
Ludvig et al.

(10) Patent No.: US 6,497,699 B1
(45) Date of Patent: Dec. 24, 2002

(54) HYBRID NEUROPROSTHESIS FOR THE TREATMENT OF BRAIN DISORDERS

(75) Inventors: Nandor Ludvig, Forest Hills, NY (US); Lorant Kovacs, Mt. Kisco, NY (US)

(73) Assignee: The Research Foundation of State University of New York, Albany, NY (US)

( * ) Notice: Subject to any disclaimer, the term of this patent is extended or adjusted under 35 U.S.C. 154(b) by 134 days.

(21) Appl. No.: 09/634,172

(22) Filed: Aug. 9, 2000

(51) Int. Cl.[7] ................................................. A61M 5/14
(52) U.S. Cl. ...................................... 604/891.1; 604/67
(58) Field of Search ........................... 604/890.1, 891.1, 604/892.1, 65, 66, 67, 788.01, 288.04, 93.01, 500, 503; 600/372, 373, 374, 377, 378, 382, 383, 544, 545

(56) References Cited

U.S. PATENT DOCUMENTS

| | | | |
|---|---|---|---|
| 4,280,494 A | | 7/1981 | Cosgrove et al. ........ 128/213 R |
| 4,511,355 A | * | 4/1985 | Franetzki et al. ......... 604/891.1 |
| 6,016,449 A | | 1/2000 | Fischell et al. ............... 607/45 |
| 6,094,598 A | | 7/2000 | Eisberry et al. ............ 607/116 |
| 6,128,537 A | | 10/2000 | Rise ............................. 607/45 |
| 6,134,474 A | | 10/2000 | Fischell et al. ................ 607/45 |
| 6,186,982 B1 | * | 2/2001 | Gross et al. ............. 604/891.1 |
| 6,248,080 B1 | * | 6/2001 | Miesel et al. ............ 604/891.1 |
| 6,315,769 B1 | * | 11/2001 | Peer et al. ................ 604/891.1 |

OTHER PUBLICATIONS

Ludvig, N., et al., "Cellular electrophysiological changes in the hippocampus of freely behaving rats during local microdialysis with epileptogenic concentration of N–methyl–D–aspartate", *Brain Res Bull*. 51(3): 233–40 (2000).

* cited by examiner

*Primary Examiner*—Harry B. Tanner
(74) *Attorney, Agent, or Firm*—Scully, Scott, Murphy & Presser

(57) ABSTRACT

A miniature apparatus for the treatment of brain disorders is provided which is a combination of electronic and pharmacological devices placed and powered entirely within the human body. The apparatus is based on the dual, electrical—molecular, nature of intercellular communication in the brain. The hybrid neuroprosthesis monitors the electrical activity of a dysfunctioning brain area, analyzes the incoming electrical signals, and delivers drug molecules into the dysfunctioning area to correct its function. The apparatus delivers drugs into the brain in such a way that the timing and duration of the drug deliveries are determined by the brain's own electrical activity. The hybrid neuroprosthesis includes (a) an electrophysiological recording electrode implanted in a dysfunctioning brain site, (b) a miniature electrical signal conditioner to amplify, filter and digitize the incoming electrophysiological signals, (c) a cannula or catheter implanted in the dysfunctioning brain site, (d) a miniature, refillable pump for driving drug solutions through the cannula or catheter, (e) a microcontroller which analyzes on-line the digitized electrophysiological signals and either activates or inactivates the pump on the basis of the analyzed electrophysiological data, (f) a miniature radiotelemetry system which provides data transfer between the apparatus and the outside world, and (g) a rechargeable power supply to power the components of the apparatus. The recording electrode can be complemented with a neurochemical sensor to transmit not only electrophysiological but also neurochemical information from the dysfunctioning brain area to the microcontroller. The components of the apparatus are encapsulated in medical grade silicon.

45 Claims, 5 Drawing Sheets

1 MIN

HYBRID NEUROPROSTHESIS FOR THE TREATMENT OF BRAIN DISORDERS

BACKGROUND OF THE INVENTION

1. Field of the Invention

The present invention relates generally to the treatment of brain disorders, and more particularly, to a hybrid neuroprosthesis apparatus implanted subcutaneously in a human subject.

2. Prior Art

At the dawn of the year 2000, effective therapy is still unavailable for the treatment of Alzheimer's disease and other degenerative disorders, stroke is still the third leading cause of death in the United States after heart disease and cancer, and currently marketed drugs are still ineffective in about 60% of patients with complex partial seizures. These few examples may demonstrate that the challenges for neurology and psychiatry in the new century will be as enormous as the achievements of these medical fields in the past one. New therapeutic strategies are needed, which capitalize on the progress in drug research, molecular biology, computer technology and electronics. Constructing neuroprosthetic devices is part of these efforts.

The first generation of successful neuroprosthesis included diaphragm pacing devices to stimulate the phrenic nerve in patients with respiratory paralysis, the Neurocybernetic Prosthesis for seizure control via vagus nerve stimulation, and cochlear implants for acoustic nerve stimulation in individuals with hearing loss. A second generation of neuroprostheses, designed to restore sensory and motor functions are under development in various laboratories. A common feature of these existing and experimental neuroprosthetic devices is that they stimulate the neural tissue electrically.

However, the neurons of the brain are not merely living electronic machines. While these cells indeed transmit information to other neurons with the use of purely electrical tools referred to as "action potentials", the generation and spacing of action potentials are regulated by molecular mechanisms. In fact, these mechanisms are sophisticated interplays of a large number of intra- and extracellular molecular systems. Thus, the neurons work as molecular-electronic computers, as they process their inputs with molecular mechanisms in order to generate electrical outputs.

The hybrid neuroprosthesis device of the present invention is essentially the translation of the dual: molecular-electronic nature of neurons into a medical device. The term "hybrid neuroprosthesis" refers to a subcutaneously implanted miniature apparatus which simultaneously acts as an electrophysiological data recorder and a drug delivery means such as a pump. This allow it to monitor the electrical activity of a dysfunctioning brain area and to correct the dysfunction by delivering drugs into the environment of the abnormal neurons.

Accordingly, the hybrid neuroprosthesis of the present invention fundamentally differs from all prior neuroprostheses, as the hybrid neuroprosthesis aims to correct neural dysfunctions pharmacologically, and not electrically. The advantage of the hybrid neuroprosthesis approach is that with drugs neuron- and synapse-specific actions can be achieved, which is difficult to accomplish with electrical stimulations.

The hybrid neuroprosthesis of the present invention also differs from the intracerebral drug delivery technologies of the prior art. No prior intracerebral drug delivery systems, including drug-loaded ethylene vinyl acetate copolymer (EVAc) rods, are able to monitor the electrical activity of the targeted brain tissue. As a consequence, no feed-back is obtained from the targeted tissue. This may lead to too high, therefore damaging, or too low, therefore ineffective, drug concentrations. No prior intracerebral drug delivery systems can apply the drug solutions periodically, only when this intervention is necessary.

Indeed, a device is needed which is able to monitor the electrical activity of a dysfunctioning brain area without interfering with the patient's daily life, yet also being able to deliver drugs into the dysfunctioning brain area: precisely when it is necessary. The hybrid neuroprosthesis device of the present invention satisfies this need, especially since the device can also be extended to monitoring not only the electrical but also the neurochemical activity of the dysfunctioning brain area and to deliver drugs into this area in response to either the neurochemical signals, or the electrical signals, or both.

SUMMARY OF THE INVENTION

Therefore, it is an object of the present invention to provide apparatus and methods for the treatment of brain disorders which overcomes the problems of the prior art.

It is a further object of the present invention to provide apparatus and methods for the treatment of brain disorders which stimulates brain tissue by pharmacological stimulation.

It is yet a further object of the present invention to provide apparatus and methods for the treatment of brain disorders which can be used in controlled human studies.

It is yet a further object of the present invention to provide apparatus and methods for the treatment of brain disorders for analyzing neuronal firing in natural circumstances, during behavior.

It is yet a further object of the present invention to provide apparatus and methods for the treatment of brain disorders in which a delivered drug solution does not affect the cells of the whole body which can drastically change the subject's behavior.

It is still yet a further object of the present invention to provide apparatus and methods for the treatment of brain disorders which regulates intracerebral drug delivery.

Accordingly, an apparatus for the treatment of brain disorders in a subject is provided. The apparatus comprises: a drug delivery means implanted in the subject for delivering at least one drug solution to the brain of the subject; a drug driving means that drives the at least one drug solution to the drug delivery means; a recording electrode implanted in the brain for outputting an electrical signal characteristic of an electrical activity of the brain; and a microcontroller for controlling the drug driving means on the basis of the electrical signal. Preferably, the entire apparatus is subcutaneously disposed in the subject. Preferably, the recording electrode is complemented with a sensor to detect neurochemical signals such as neurotransmitter release or other molecular events. Alternatively, the recording electrode is replaced by a neurochemical sensor.

The drug delivery means is preferably a cannula, such as a multi-port cannula having a plurality of ports, each port delivering the drug solution to a corresponding portion of the brain or an intraventricular cannula for delivering the drug solution to a substantial portion of the brain. Alternatively, the drug delivery means can be a catheter, microdialysis probe, or other drug ejector device. The drug delivery means is implanted in the brain of the subject or in the ventricular system of the subject.

The drug driving means is preferably a pump, that includes a drug reservoir for holding the at least one drug solution and which is also preferably subcutaneously disposed in the subject and is externally accessible on the surface of the skin for periodic refilling. Alternatively, the drug driving device can be a microcapillary device, nanotube, microtube, microfabricated pathway using electrokinetic force, or other components.

The apparatus preferably further comprises an electrical signal conditioner disposed between the recording electrode and the microcontroller for amplifying, filtering and digitizing the recorded electrical signals from the brain and inputting the conditioned signals to the microcontroller, wherein the electrical signal conditioner is also preferably subcutaneously disposed in the subject.

The microcontroller is preferably equipped with a microprocessor, to analyze the electrophysiological data stream from the electrical signal conditioner and regulate the drug driving means accordingly. Alternatively, the microcontroller can be a digital signal processor (DSP), a programmable logical array (PLA), a programmable logical device (PLD), an application-specific integrated circuit (ASIC), or other similar device. The processor can be equipped with a transmitter to transmit, preferably via a communication system, the analyzed electrophysiological signals to outside of the body for more advanced human and computer analysis. The processor is preferably further equipped with a receiver to receive, preferably via a communication system, human and computer commands from outside of the body.

The apparatus still further comprises a power source, such as a battery, for supplying power to the drug driving device, the microcontroller and the electrical signal conditioner. The battery is preferably a NiMH or Lithium-ion battery which is also subcutaneously disposed in the subject and is rechargeable from the outside of the body from an electromagnetic or optical power source. Alternatively, the power source is a subcutaneous current generator.

In a preferred configuration of the apparatus, the microcontroller, the drug driving means, the electrical signal conditioner and the battery are housed in a single container subcutaneously disposed in the subject. The container is preferably an elastomer case fabricated from medical grade silicon and is subcutaneously disposed in the subject at the base of the brain and back of the neck. Alternatively, the microcontroller, the drug driving means, the electrical signal conditioner and the power source can be housed in individual containers, located in distant body parts under the skin, and are interconnected via subcutaneous tunneling.

Also provided are methods for the treatment of brain disorders with the apparatus of the present invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of subjects, it is particularly useful in the environment of human subjects. Therefore, without limiting the applicability of the invention to human subjects, the apparatus and methods of the present invention will be described in such an environment.

The term "hybrid neuroprosthesis" as used herein refers to a microprocessor-controlled, intracerebrally implanted drug delivery device, in which the timing and duration of the drug deliveries are determined by the implanted brain tissue's own electrical activity. Thus, the device is a "hybrid" of pharmacological and electrophysiological instruments. The pharmacological components are: (1) a drug delivery device such as a cannula, catheter, or microdialysis probe chronically implanted in the ventricular system or in the brain tissue, and (2) a miniature, subcutaneously placed drug reservoir/drug driving means, which can be periodically refilled. The electrophysiological components are: (1) a recording electrode chronically implanted in the brain, and (2) a miniature, subcutaneously placed electrical signal conditioner. A processor, alternatively referred to as a microcontroller, placed in close proximity to these components, both analyzes the electrophysiological data and controls the drug reservoir/drug driving means. All of these components are powered by a nearby power supply, such as a battery, and sealed in a biocompatible case.

Figure 1A:
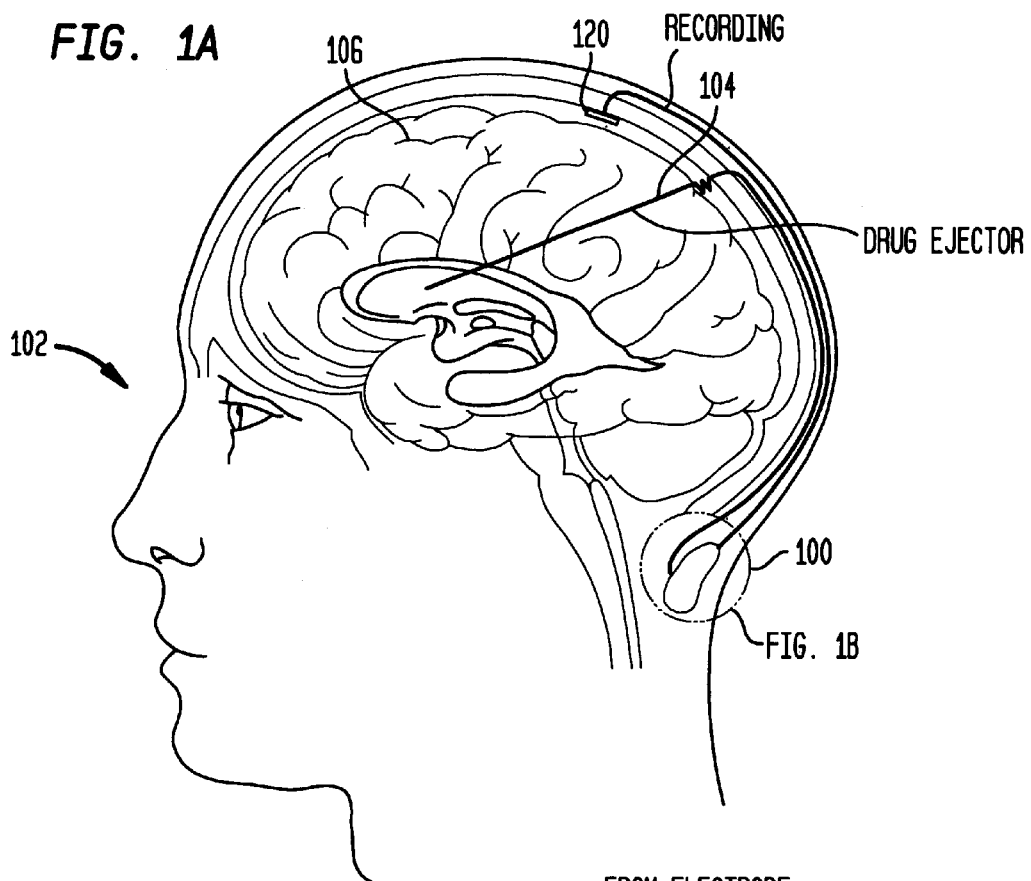
FIG. 1A illustrates the hybrid neuroprosthesis of the present invention subcutaneously disposed in a subject.
Figure 1B:
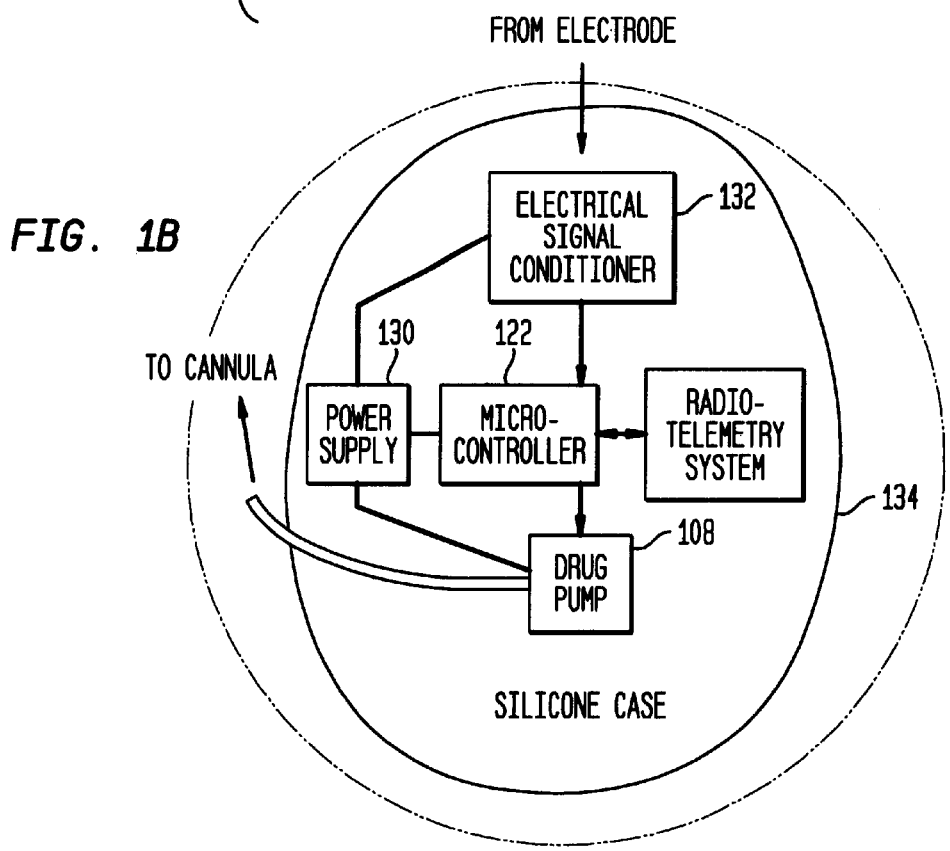
FIG. 1B illustrates an enlarged view of the hybrid neuroprosthesis of FIG. 1A.
Figure 1C:
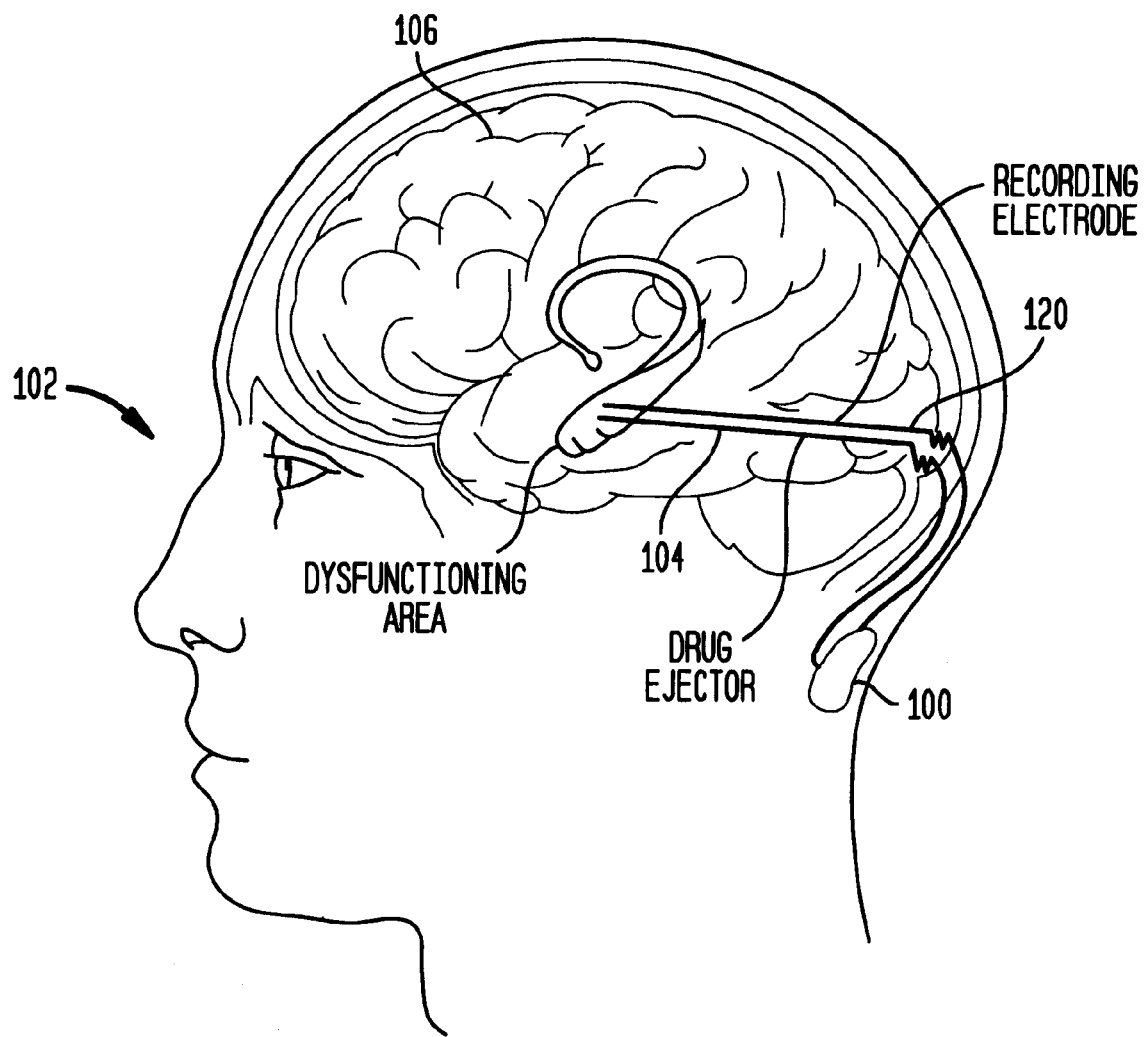
FIG. 1C illustrates an alternative configuration of the hybrid neuroprosthesis of the present invention.

Referring now to FIGS. 1A, 1B, and 1C in combination, there is illustrated an apparatus for the treatment of brain disorders in a subject, the apparatus being generally referred to by reference numeral 100, the subject by reference numeral 102. The subject is illustrated as a human by way of example only, and not to limit the scope or spirit of the invention in any way. Although, the apparatus is ultimately intended for treatment of brain disorders in humans, testing on laboratory animals or primates is not precluded from the scope of the present invention.

The apparatus 100 of the present invention includes a drug delivery means shown generally at reference numeral 104. The drug delivery means is implanted in the subject 102 for delivering at least one and possibly several drug solutions to a point of interest in the brain 106 of the subject 102. The drug delivery means 104 can be a cannula such as a multi-port cannula having a plurality of ports, each port delivering the drug solution to a corresponding portion of the brain 106 or an intraventricular cannula for delivering the drug solution to a substantial portion of the brain 102. Other types of cannulas known in the medical arts can also be used to deliver the drug solution to the point of interest in the brain 106. The drug delivery means 104 can alternatively be a catheter, a microdialysis probe, or other drug ejector device.

The drug delivery means 104 can be either implanted directly in the brain 106 of the subject or in the ventricular system of the subject. The implantation directly into the brain 106 is preferred because the time lag between the introduction of the drug solution and any effects therefrom are minimized. Cannulas, catheters, and microdialysis probes and the use and implantation thereof are well known in the medical arts and thus, a detailed description of them is omitted.

The apparatus 100 of the present invention also includes a drug driving means 108, such as a pump which is preferably subcutaneously disposed in the subject 102 for delivering the drug solutions to the drug delivery means 104. The drug driving means and drug delivery means are adapted to each other with appropriate tubing and fittings which are well known in the medical arts. Preferably, the tubing and fittings are also subcutaneously disposed in the subject 102.

Figure 3:
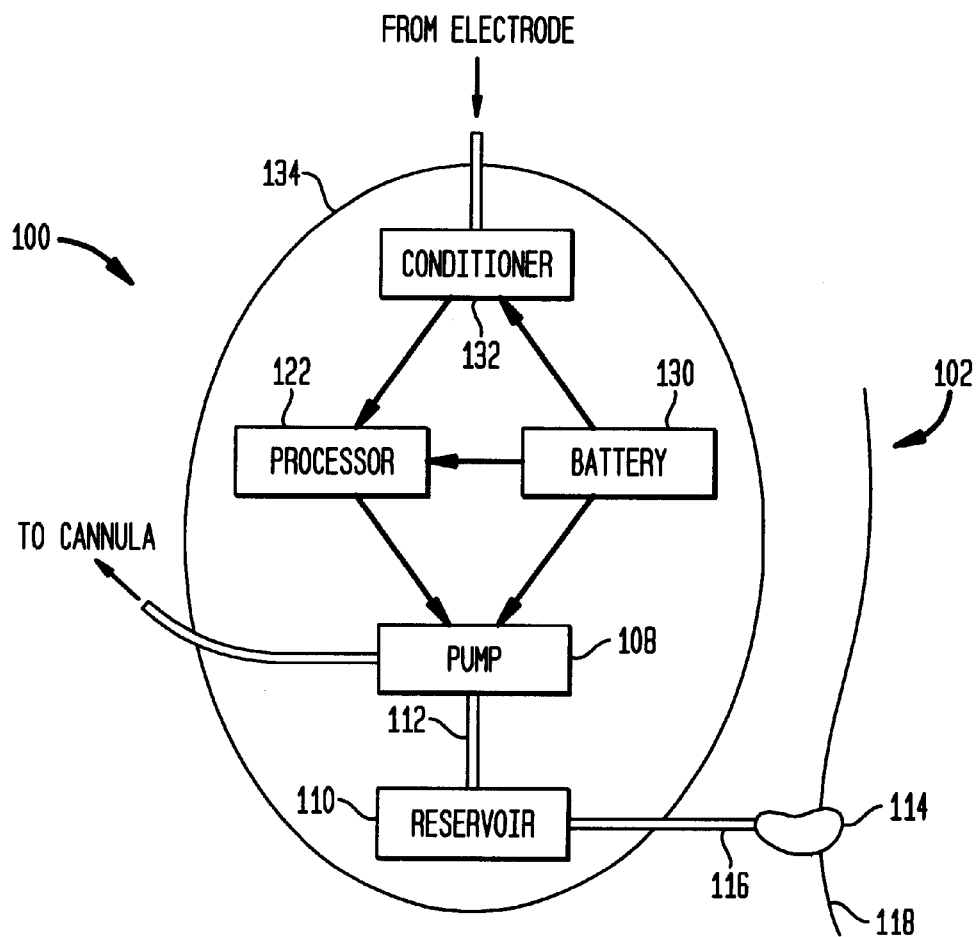
FIG. 3 illustrates an alternative version of the hybrid neuroprosthesis of FIG. 1B.

Referring now to FIG. 3, the drug driving means 108 preferably also includes a drug reservoir 110 for holding a corresponding drug solution. The drug reservoir 110 is also preferably subcutaneously disposed in the subject 102 proximate to the drug driving means 108. The drug driving means 108 and drug reservoir 110 are in fluid communication with each other by way of appropriate fittings and tubing 112 such that the drug driving means 108 can draw the drug solution from the drug reservoir 110 upon operation of the drug driving means 108.

The drug reservoir 110 can be initially filled with the drug solution prior to being implanted in the subject 102, in which case a surgical procedure is necessary if the drug reservoir needs refilling. However, the drug reservoir 110 preferably includes a reservoir input 114 for supplying the drug solution to the drug reservoir. The reservoir input 114 is in fluid communication with the drug reservoir through appropriate fittings and tubing 116 and externally accessible on a surface of the skin 118 of the subject 102 for periodic refilling. The reservoir input 114 is preferably a self-sealing syringe fitting known in the medical arts but can be any type of fitting known in the medical arts which provides such external access.

Alternatively, the drug driving device can be a microcapillary device, nanotube, microtube, microfabricated pathway using electrokinetic force, or other components, and can be placed in body parts distant from the rest of the hybrid neuroprosthesis.

Referring back to FIGS. 1A, 1B, and 1C in combination, the apparatus 100 of the present invention also includes a recording electrode 120 implanted in the brain 106 for outputting an electrical signal characteristic of an electrical activity of the brain 102. Although implantation of the recording electrode 120 is described as being in the brain 106, as shown in FIG. 1C, this phraseology is also intended to cover implantation of the recording electrode 120 on the brain 106 or in proximity to the surface of the brain 106, as shown in FIG. 1A, depending upon the type of recording electrode 120 utilized. The recording electrode 120 is preferably an EEG electrode which outputs a signal 121 (FIG. 2) corresponding to the EEG waves in the point of interest in the brain 106 per unit time. The recording electrode can be an extracellular recording electrode and can be complemented with a sensor to detect neurochemical signals such as neurotransmitter release or other molecular events.

The apparatus 100 of the present invention further includes a microcontroller 122 which is preferably subcutaneously disposed in the subject 102 for controlling the drug driving means 108 on the basis of the electrical signal 121 from the probe 120.

Figure 2:
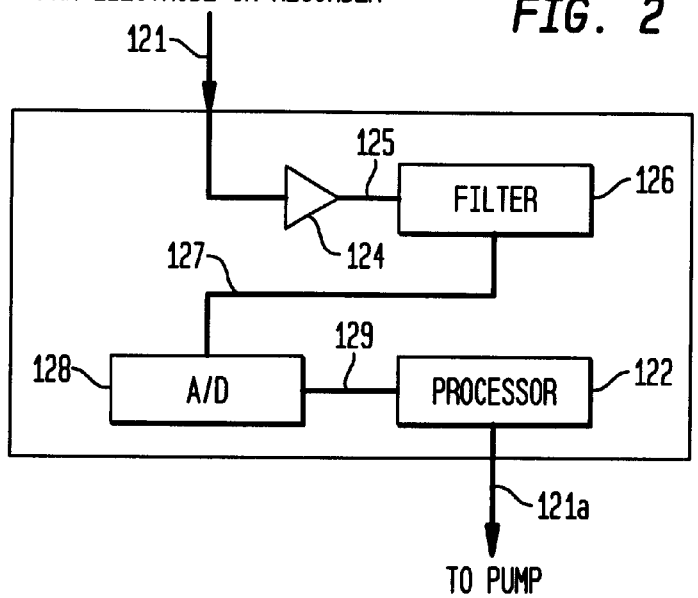
FIG. 2 illustrates the schematic diagram of a preferred implementation of the electrical signal conditioner—microcontroller unit of FIG. 1B.

Referring now to FIGS. 2 and 3, the microcontroller 122 preferably is accompanied by an electrical signal conditioner 132 for amplifying, filtering, and digitizing the recorded electrical signals from the brain and inputting the conditioned signals to the microcontroller. The electrical signal conditioner 132 includes an amplifier 124 for amplifying the signal 121 from the electrode 120 (see FIGS. 1a and 1c), a filter 126 for filtering the amplified signal 125, and an analog to digital (A/D) converter 128 for converting the filtered signal 127 to a digital signal 129. The digital signal 129 is input to the microcontroller 122 which outputs a signal 121a to control the operation of the drug driving means 108 (see FIGS. 1b and 3). The filtered signal is a more reliable indication of the brain characteristic being sensed and does not include any noise from external sources, such as a cellular phone.

The microcontroller 122 is preferably a microprocessor, to analyze the electrophysiological data stream from the electrical signal conditioner and regulate the drug delivery means accordingly. Alternatively, the microcontroller can be a digital signal processor (DSP), programmable logical array (PLA), a programmable logical device (PLD), or application-specific integrated circuit (ASIC). The microcontroller 122 is preferably equipped with a transmitter to transmit, preferably via a communication system such as a radiotelemetry system, the analyzed electrophysiological signals to outside of the body for more advanced human and computer analysis. The microcontroller is yet preferably further equipped with a receiver to receive, preferably via a radiotelemetry or other communication system, human and computer commands from outside of the body.

Referring back to FIGS. 1A, 1B, and 1C in combination, the apparatus 100 of the present invention preferably also includes a power source 130, such as a battery, for supplying power to the drug driving means 108, microcontroller 122, and any other electrical components such as the electrical signal conditioner 132. The battery 130 is also preferably subcutaneously disposed in the subject 102. The power source 130 is preferably a NiMH or Lithium-ion battery which is also subcutaneously disposed in the subject and is rechargeable from the outside of the body from an electromagnetic or optical power source. Alternatively, the power source 130 is a subcutaneous current generator which taps the energy of the body.

The electrical signal conditioner 132 of the present invention preferably also further comprises a recorder disposed between the recording electrode 120 and the microcontroller 122 for recording the electrical signal 121 from the brain 106 and inputting the recorded signal to the microcontroller 122. The recordation of the signal 121 from the recording electrode 120 allows for future analysis of the signals over time and a comparison of such with other concurrent or subsequent observations such as behavior of the subject. The conditioner/recorder 132 is also preferably subcutaneously disposed in the subject 102.

Some or all of the aforementioned components of the apparatus 100 of the present invention with the exception of the working ends of the recording electrode and drug delivery means are preferably housed in a single container 134 subcutaneously disposed in the subject 102. Preferably, the recorder, battery, drug driving means, electrical signal conditioner, and microcontroller are all housed within the container 134 in a compact miniature assembly. The container 134 is preferably a biocompatible elastomer case and more preferably is fabricated from medical grade silicon. Although the container 134 can be subcutaneously placed in a number of places in the subject, the preferable location for the subcutaneous placement of the container 134 is at the base of the brain 106 and back of the neck, as is illustrated in FIGS. 1A and 1C. Alternatively, the microcontroller, the drug driving means, the electrical signal conditioner/recorder 132, and the power source can be housed in individual containers, located in distant body parts under the skin, and are interconnected via subcutaneous tunneling.

Figure 4A:
FIGS. 4A and 4B illustrate normal and abnormal neuronal firing patterns in the rat hippocampus, respectively.
Figure 4B:

The operation of the apparatus 100 of the present invention will now be described with reference to the Figures. The recording electrode 120 senses a characteristic of the brain, e.g., an electrical characteristic of the brain such as the rate of neuron cell firings per unit time, and outputs an electrical signal 121 corresponding to that characteristic. The conditioner/recorder 132 conditions and/or records the signals over time and passes the signal to the microcontroller 122 which analyzes the signal based on a certain criteria and controls the drug driving means 108 accordingly. For instance, upon the detection by the recording electrode 120 that the rate of neuron cell firings has increased over a predetermined threshold (FIG. 4B), the drug driving means 108 is controlled by the microcontroller 122 to turn on and deliver the drug solution(s) from the drug reservoir(s) 110. The drug driving means 108 may deliver a predetermined amount of drug solution or continue to deliver the drug solution until the detected characteristic returns to a level below the predetermined threshold (FIG. 4A). The response to the drug solution is recorded by the conditioner/recorder 132 and analyzed.

The apparatus of the present invention can be used for the management of intractable temporal lobe epilepsies, which are currently treated by surgical removal of the epileptogenic tissue. The recording electrodes can monitor the electrophysiological activity of the epileptogenic focus (the area that generates seizures and contribute to interictal spiking), and from the recorded electrical signals the subcutaneously implanted microcontroller can recognize the initiation of an EEG seizure and activate the drug driving means to deliver an antiepileptic drug solution directly into the pathophysiological tissue of the brain.

Another application for the apparatus of the present invention is the intracerebroventricular administration of drug combinations, continuously adjusted by simultaneous electrophysiological monitoring, in patients with Alzheimer's disease. In rats, chronic intracerebroventricular infusion of the phoshoprotein phosphatase inhibitor, okadaic acid, induces histopathological changes in the hippocampus and neocortex that resembles those that occur in Alzheimer's disease. This indicates that the neural circuitries involved with Alzheimer's disease can be affected by drugs administered into the ventricles. If so, beneficial effects are also inducible in this disease via ventricular drug administrations, for example, with the use of a hybrid neuroprosthesis such as the apparatus of the present invention. The drug solution, ejected by the hybrid neuroprosthesis for the treatment of Alzheimer's disease may contain several small molecules, peptides and proteins which act, in concert, on neurotransmitter receptors, ion channels, second messengers, genes, as well as on abnormal proteins such as hyperphosphorylated MAP tau in order to specifically increase the engram-creating firing rates of normal neurons while decrease the toxic load of abnormal neurons.

The apparatus of the present invention is also useful in the management of Parkinson's disease. There are those in the art who have reported clinical improvements in patients with Parkinson's disease following the grafting of human embryonic dopamine-rich mesencephalic tissue unilaterally into the putamen. Thus, the treatment was achieved with implanting the dopamine-rich tissue at a single occasion, and without monitoring the electrical activity of the grafted area. The apparatus of the present invention can offer multiple drug administrations into the putamen, regulated by local electrophysiological recordings. The viability of the hybrid neuroprosthesis strategy in the management of other brain disorders, especially in that of stroke, is also possible. The above brain disorders are given by way of examples only, and not to limit the scope of the invention in any way. Those of skill in the art will recognize that the apparatus of the present invention may be useful for a great number of brain disorders.

The apparatus of the present invention is useful for delivering drugs into a specific, pathophysiologically functioning brain site. However, brain disorders usually involve not one but several interconnected regions that function abnormally. Therefore, localized drug deliveries may not be able to correct or reverse diffuse pathophysiological processes. This problem can be resolved with the use of a multiport cannula as the drug delivery means 104, which can release drugs along their axis into many brain sites, or intraventricular cannulas which can provide widespread drug administrations into the brain 106. Multiple drug reservoir-pump units, each having a cannula to a discrete brain area, can also be used to achieve widespread pharmacological effects in the brain.

Figure 5:
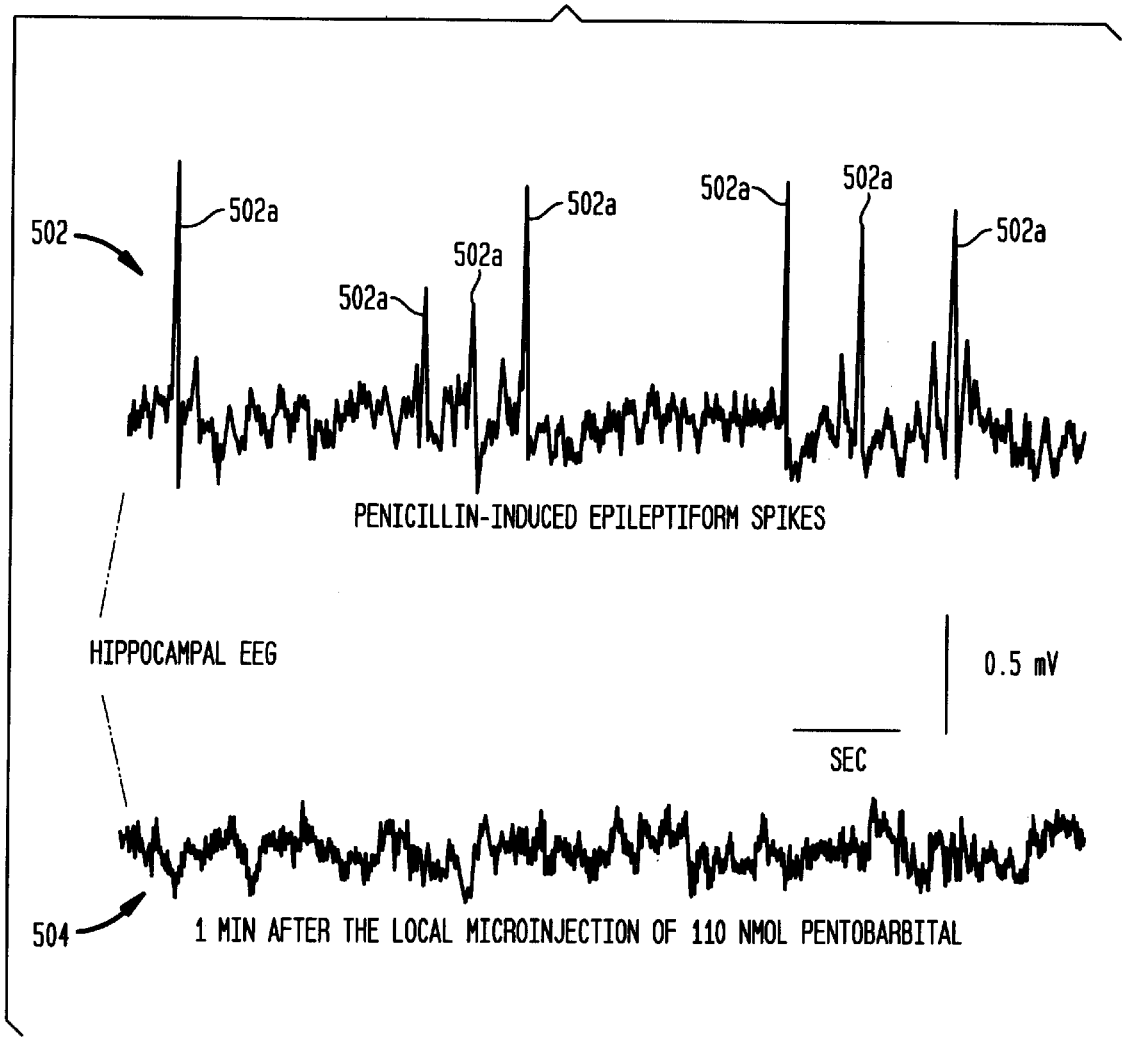
FIG. 5 presents an experimental model for the hybrid neuroprosthesis concept, showing EEG recordings from the epileptogenic hippocampus of a rat before and after the microinjection of an antiepileptic drug solution directly into the dysfunctioning hippocampal area.

Referring now to FIG. 5, there are illustrated electroencephalogram (EEG) traces 502, 504 from the hippocampus of a rat, where the hippocampus was experimentally made epileptogenic. The epileptogenic focus was created in the hippocampus of the rat by the intrahippocampal injection of 150 units of penicillin G. The upper trace 502 shows the EEG of the rat 16 hours after the creation of the focus, note the high amplitude epileptiform interictal spikes 502a on the upper trace recording 502. The lower trace 504 shows the hippocampal EEG activity of the rat one minute after the injection of pentobarbital, an antiepileptic drug, into the epileptogenic focus. Note the complete cessation of the epileptiform electrical activity in the lower trace recording 504. This experimental model demonstrates the correctness of the hybrid neuroprosthesis concept, namely, that the abnormal activity of a dysfunctioning brain area can be corrected by the injection of the proper drug into the area of dysfunction.

In summary, the apparatus of the present invention uses an intracerebrally implanted electrode, cannula units, connected to a subcutaneously implanted microcontroller which analyzes the recorded electrophysiological signals and activates a nearby drug driving means, such as a pump, to deliver drug solutions through a drug delivery means 104 such as a cannula. In this way, finely controlled intracerebral drug deliveries into a malfunctioning brain area can be achieved at the moment when abnormal electrical activity occurs in the malfunctioning brain area. Such an apparatus is a useful addition to the repertoire of future neuroprosthesis.

While there has been shown and described what is considered to be preferred embodiments of the invention, it will, of course, be understood that various modifications and changes in form or detail could readily be made without departing from the spirit of the invention. For instance, it should be apparent to those skilled in the medical arts that a plurality of recording electrodes 120 and drug delivery means 104 can be utilized without departing from the scope or spirit of the present invention. In such a configuration, each of the plurality of recording electrodes 120 can input a signal to a single microcontroller 122 which can control a separate drug driving means 108 for each drug delivery means 104 (i.e., each of a plurality of cannulas and/or catheters). Alternatively, a single drug driving means 108 can be used to deliver the drug solution to all of the drug delivery means 104. It is also understood that the recording electrode can be readily complemented with a neurochemical sensor to provide, after appropriate molecule concentration—electrical current conversion, additional electrical input to the microcontroller.

It is therefore intended that the invention be not limited to the exact forms described and illustrated, but should be construed to cover all modifications that may fall within the scope of the appended claims.

What is claimed is:

1. An apparatus for the treatment of brain disorders in a subject, the apparatus comprising:
   a drug delivery means implanted in the subject for delivering at least one drug solution to the brain of the subject;
   a drug driving means for delivering the at least one drug solution to the drug delivery means;
   a recording electrode implanted in the brain for outputting a first electrical signal characteristic of an electrical activity of the brain;
   a neurochemical sensor for detecting neurochemical signals of the brain and converting the neurochemical signals to a second electrical signal; and
   a microcontroller controlling the drug driving means on the basis of the first and second electrical signals.

2. The apparatus of claim 1, wherein the drug driving means is subcutaneously disposed in the subject.

3. The apparatus of claim 1, wherein the microcontroller is subcutaneously disposed in the subject.

4. The apparatus of claim 1, wherein the drug delivery means is a cannula.

5. The apparatus of claim 4, wherein the cannula is a multi-port cannula having a plurality of ports, each port delivering the at least one drug solution to a corresponding portion of the brain.

6. The apparatus of claim 4, wherein the cannula is a intraventricular cannula for delivering the at least one drug solution to a substantial portion of the brain.

7. The apparatus of claim 4, wherein the drug delivery means is a catheter.

8. The apparatus of claim 1, wherein the drug delivery means is implanted in the brain of the subject.

9. The apparatus of claim 1, wherein the drug delivery means is implanted in the ventricular system of the subject.

10. The apparatus of claim 1, wherein the drug driving means further includes a drug reservoir for holding the drug solution.

11. The apparatus of claim 10, wherein the drug reservoir is subcutaneously disposed in the subject.

12. The apparatus of claim 11, further comprising a reservoir input for supplying the at least one drug solution to the drug reservoir, the reservoir input being in fluid communication with the drug reservoir and externally accessible on a surface of the skin of the subject.

13. The apparatus of claim 12, wherein the reservoir input is a self-sealing syringe fitting.

14. The apparatus of claim 1, wherein the recording electrode is an EEG electrode.

15. The apparatus of claim 1, wherein the recording electrode outputs a signal corresponding to a rate of neuron cell firings per unit time.

16. The apparatus of claim 1, further comprising an electrical signal conditioner disposed between the recording electrode and the microcontroller for recording the signal from the brain and inputting the recorded signal to the microcontroller.

17. The apparatus of claim 16, wherein the electrical signal conditioner is subcutaneously disposed in the subject.

18. The apparatus of claim 1, wherein the microcontroller further comprises an electrical signal conditioner having an amplifier for amplifying the signal, a filter for filtering the noise from the analog signal, and an analog to digital converter for converting the filtered analog signal to a digital signal, the digital signal being input to the microcontroller.

19. The apparatus of claim 1, further comprising a power source for supplying power to the drug driving means and microcontroller.

20. The apparatus of claim 19, wherein the power source is a rechargeable battery.

21. The apparatus of claim 20, wherein the battery is subcutaneously disposed in the subject.

22. The apparatus of claim 1, further comprising a container subcutaneously disposed in the subject for housing the microcontroller and drug driving means.

23. The apparatus of claim 17, further comprising a container subcutaneously disposed in the subject for housing the microcontroller, drug driving means, and electrical signal conditioner.

24. The apparatus of claim 21, further comprising a container subcutaneously disposed in the subject for housing the microcontroller, drug driving means, and battery.

25. The apparatus of claim 22, wherein the container is an elastomer case.

26. The apparatus of claim 25, wherein the elastomer case is fabricated from medical grade silicon.

27. The apparatus of claim 1, further comprising a neurochemical sensor for detecting neurochemical signals of the brain and converting the neurochemical signals to electrical signals, the microcontroller also analyzing the converted electrical signals from the neurochemical sensor and controlling the drug driving means on the basis thereof.

28. The apparatus of claim 1, further comprising a communication system for allowing wireless data exchange from the microcontroller to a remote location.

29. A method for treating brain disorders in a subject, the method comprising the steps of:
   implanting a drug delivery means in the subject for delivering at least one drug solution to the brain of the subject;
   subcutaneously disposing a drug driving means in the subject for delivering the at least one drug solution to the drug delivery means;
   implanting a recording electrode in the brain of the subject for outputting a first electrical signal characteristic of an electrical activity of the brain;
   implanting a neurochemical sensor in the brain for detecting neurochemical signals of the brain and converting the neurochemical signals to a second electrical signal;
   subcutaneously disposing a microcontroller in the subject; and
   controlling the drug driving means on the basis of the first and second electrical signals to deliver the at least one drug solution to the brain of the subject.

30. The method of claim 29, wherein the drug delivery means is a multi-port cannula having a plurality of ports, the method further comprising the step of delivering the drug solution to each port corresponding to a different portion of the brain.

31. The method of claim 29, wherein the drug delivery means is a intraventricular cannula, the method further comprising the step of delivering the drug solution to a substantial portion of the brain.

32. The method of claim 29, wherein the implanting of the drug delivery means comprises implanting the drug delivery means in the brain of the subject.

33. The method of claim 29, wherein the implanting of the drug delivery means comprises implanting the drug delivery means in the ventricular system of the subject.

34. The method of claim 29, further comprising the step of subcutaneously disposing a drug reservoir in the subject for holding the at least one drug solution.

35. The method of claim 34, wherein the step of subcutaneously disposing a drug reservoir in the subject further comprises disposing a reservoir input in fluid communication with the drug reservoir on a surface of the skin of the subject and further comprising the step of supplying the drug solution to the drug reservoir through the reservoir input.

36. The method of claim 29, further comprising the step of outputting the electrical signal corresponding to a rate of neuron cell firings per unit time.

37. The method of claim 29, further comprising the step of subcutaneously disposing a recorder in the subject between the recording electrode and the microcontroller for recording the signal from the brain and inputting the recorded signal to the microcontroller.

38. The method of claim 29, further comprising the steps of amplifying the signal, filtering the analog signal, and converting the filtered analog signal into digital signal being input to the microcontroller.

39. The method of claim 29, further comprising the step of subcutaneously disposing a battery in the subject for supplying power to the drug driving means and microcontroller.

40. The method of claim 29, further comprising the steps of housing the microcontroller and drug driving means in a container and subcutaneously disposing the container in the subject.

41. The method of claim 40, wherein the step of subcutaneously disposing the container in the subject comprises subcutaneously disposing the container at the base of the brain and back of the neck.

42. The method of claim 29, wherein the controlling step comprises the step of supplying power to the drug driving means to deliver drug solution to the brain of the subject when the electrical signal reaches a predetermined threshold.

43. The method of claim 42, wherein the supplying step comprises the step of continuing to supply power to the drug driving means for a predetermined time to deliver a predetermined amount of drug solution to the brain.

44. The method of claim 42, wherein the supplying step comprises the step of continuing to supply power to the drug driving means until the signal retracts from the predetermined threshold.

45. The method of claim 29, wherein the brain disorder is selected from a group consisting of stroke, epilepsy, Alzheimer's disease, and Parkinson's disease.

* * * * *